United States Patent
Yu et al.

(10) Patent No.: US 7,723,086 B2
(45) Date of Patent: May 25, 2010

(54) APPARATUS FOR ENCAPSULATING CELLS

(75) Inventors: Hanry Yu, Singapore (SG); Hai Ting Ho, Singapore (SG); Jing Zhang, Singapore (SG)

(73) Assignee: Agency for Science, Technology + Research, Centros (SG)

( * ) Notice: Subject to any disclaimer, the term of this patent is extended or adjusted under 35 U.S.C. 154(b) by 1132 days.

(21) Appl. No.: 10/869,002

(22) Filed: Jun. 16, 2004

(65) Prior Publication Data

US 2005/0282264 A1    Dec. 22, 2005

(51) Int. Cl.
C12N 11/04 (2006.01)
C12N 11/02 (2006.01)
C12N 11/10 (2006.01)
B01J 13/02 (2006.01)

(52) U.S. Cl. ............... 435/182; 435/177; 435/178; 435/179; 435/382; 435/395; 435/458; 424/424; 264/4.7; 530/817; 427/213.3

(58) Field of Classification Search ......... 435/182, 435/178, 177, 179, 382, 395, 458; 424/424; 264/4.7; 530/817; 427/213.3
See application file for complete search history.

(56) References Cited

U.S. PATENT DOCUMENTS

| | | | | |
|---|---|---|---|---|
| 5,286,495 | A * | 2/1994 | Batich et al. | 424/490 |
| 5,418,154 | A * | 5/1995 | Aebischer et al. | 435/182 |
| 5,462,866 | A | 10/1995 | Wang | 435/174 |
| 5,620,883 | A | 4/1997 | Shao et al. | 435/174 |
| 5,693,514 | A * | 12/1997 | Dorian et al. | 435/178 |
| 6,458,296 | B1 | 10/2002 | Heinzen et al. | 264/9 |
| 6,531,156 | B1 | 3/2003 | Clark et al. | 424/489 |
| 6,599,274 | B1 | 7/2003 | Kucharczyk et al. | 604/264 |
| 6,645,488 | B2 | 11/2003 | Xue et al. | 424/93.7 |
| 6,649,384 | B2 | 11/2003 | Walsh et al. | 435/178 |
| 7,354,764 | B2 * | 4/2008 | Bader | 435/395 |
| 2003/0093034 | A1 | 5/2003 | Chang et al. | 604/190 |
| 2003/0204171 | A1 | 10/2003 | Kucharczyk et al. | 604/264 |
| 2003/0210985 | A1 * | 11/2003 | Feygin et al. | 417/46 |

(Continued)

FOREIGN PATENT DOCUMENTS

CA    1215922    12/1986

(Continued)

OTHER PUBLICATIONS

Aug. 1, 2005 International Search Report and Written Opinion of the International Searching Authority for International Application No. PCT/SG2005/000175 (9 pages).

(Continued)

*Primary Examiner*—William H Beisner
*Assistant Examiner*—Nathan A Bowers
(74) *Attorney, Agent, or Firm*—Stout, Uxa, Buyan & Mullins, LLP; Carlos A. Fisher

(57) ABSTRACT

An apparatus for encapsulating cells is disclosed. According to one embodiment, the apparatus includes an indirect-pumping dispenser for dispensing a cell suspension into an encapsulation solution through an outlet of the dispenser. The apparatus also includes a dipping mechanism that is attachable to the outlet of the dispenser. The dipping mechanism is adapted to dip the dispenser outlet in the encapsulation solution to allow the cell suspension dispensed thereat to come into contact with the encapsulation solution.

31 Claims, 7 Drawing Sheets

U.S. PATENT DOCUMENTS

2005/0158395 A1* 7/2005 Zimmermann et al. ...... 424/490
2005/0175978 A1* 8/2005 Ramasubramanian .......... 435/2

FOREIGN PATENT DOCUMENTS

| WO | 9316687 | 9/1993 |
| WO | 9631199 | 10/1996 |
| WO | 00/56861 | 9/2000 |
| WO | 01/03756 | 1/2001 |
| WO | 03/006089 | 1/2003 |

OTHER PUBLICATIONS

Chia et al., "Hepatocyte encapsulation for enhanced cellular functions", Tissue Engineering, 6(5):481-495 (2000).

Uludag et al., "Technology of mammalian cell encapsulation", Advanced Drug Delivery Reviews, 42:29-64 (2000).

* cited by examiner

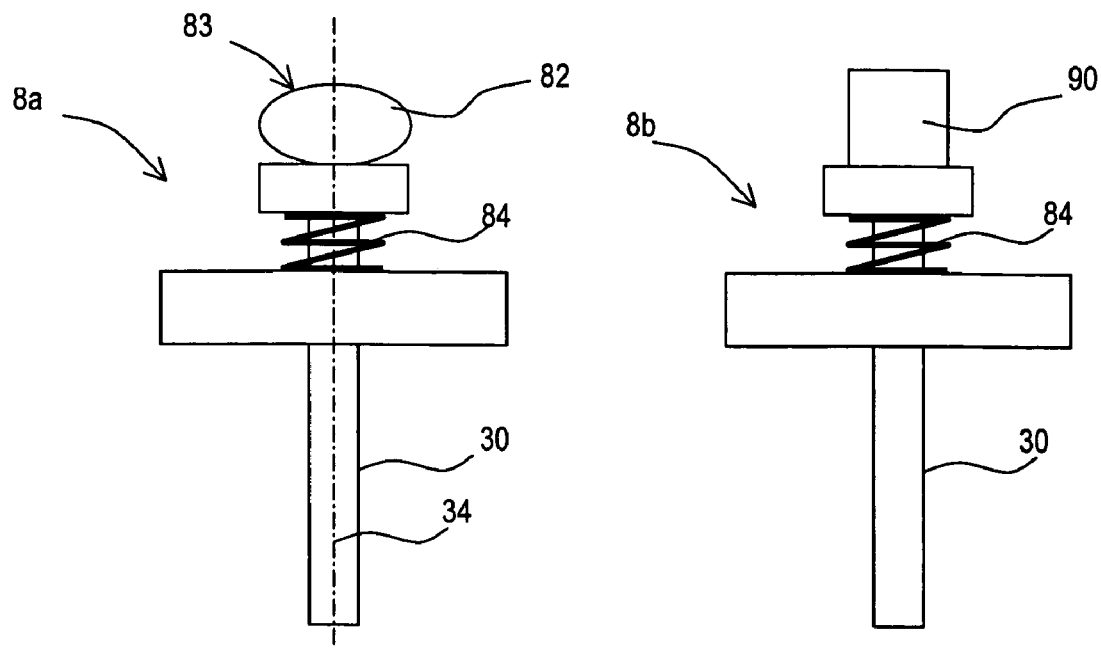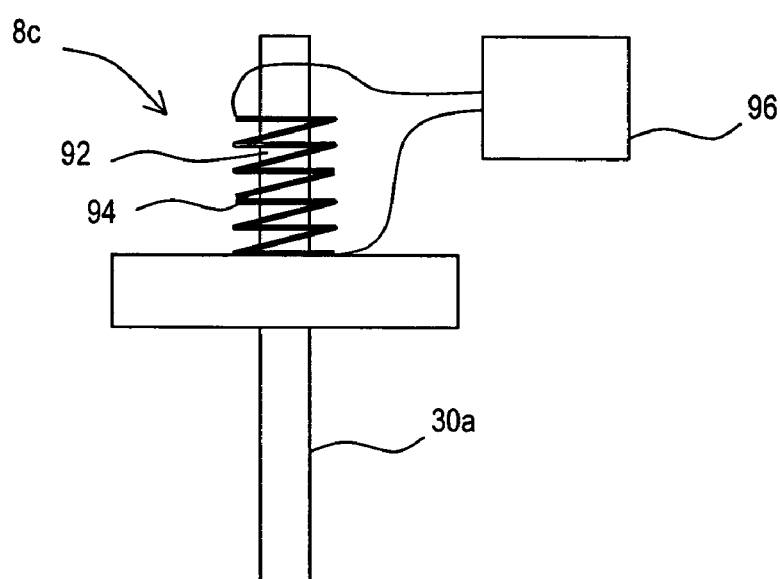
FIGURE 4
FIGURE 5
FIGURE 6

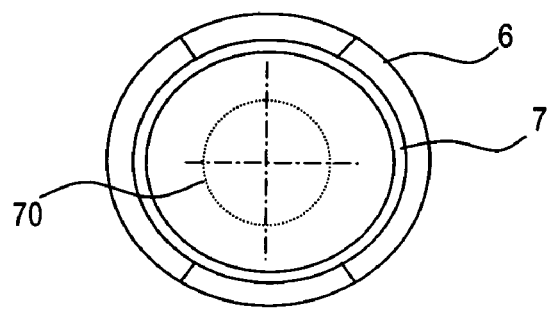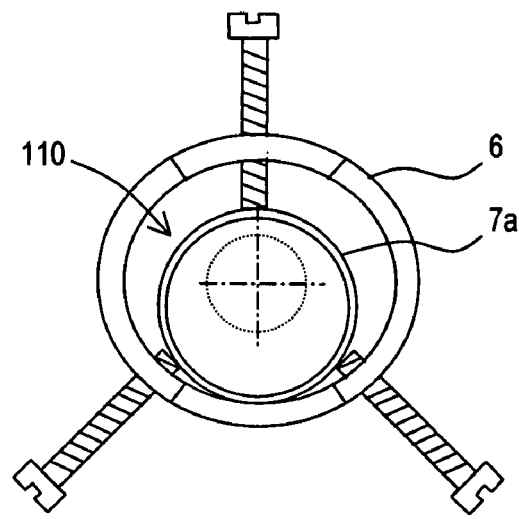
FIGURE 10
FIGURE 11
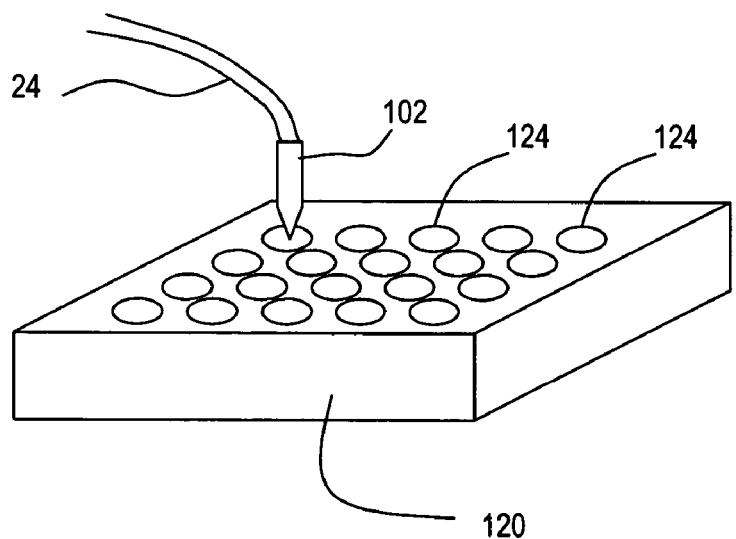
FIGURE 12

APPARATUS FOR ENCAPSULATING CELLS

BACKGROUND

The invention relates to an apparatus for encapsulating cells, more specifically, for encapsulating cells, such as animal cells, to form small capsules.

The encapsulation of living cells, such as animal cells including human cells, is of great significance in biotechnology and medicine, for example for immobilization purposes (see, for example, Uludag, H. et al., Advanced Drug Delivery Reviews 42 (2000), 29-64). For instance, body cells such as hepatocytes in microcapsules composed of ultrathin, semi-permeable membranes can have applications, for example, in hybrid bioartificial liver-assisted devices. Such applications involve containment of encapsulated hepatocytes in a bioreactor that is implanted in patients with liver failure (see Chia et al., Tissue Engineering 6(5): 481-95). Another application is the encapsulation of islet cells for the production of insulin (see U.S. Pat. No. 5,462,866 for example). To mention a third example, erythropoetin producing kidney cells have been suggested for the treatment of anemia.

Encapsulation of cells in polymers, such as alginate, through an alginate-gelation complex coacervation method has been extensively studied. In this method, alginate, which is a glycuranan extracted from the brown seaweed algae, can be chelated by calcium to form a gel. Early results obtained with an alginate-polylysine system were inconsistent and thus inconclusive because of the uncontrollable purity of the alginate, and the incorporation of cells within the formed external membrane. Consequently, a two-step encapsulation scheme was used. The calcium alginate gel droplets were incorporated into larger alginate gel spheres and then reacted with a poly-amino acid such as poly-L-lysine to form a semi permeable membrane. Sodium citrate was then added to liquefy the interior to form microcapsules. Unfortunately, sodium citrate had adverse effect on the bioactivity of hepatocytes, and the water-soluble alginate and polylysine were found to be not particularly biocompatible as individual polymers. As a result, other alternatives, such as collagen, have been investigated to see if they are better substrates for cellular functions than alginate.

Manual encapsulation involves extrusion of a charged stream of cell mixture or suspension into an encapsulation solution of an opposite charge. Manual encapsulation works but the size of capsules produced is inconsistent and the process is time consuming.

U.S. Pat. No. 5,462,866 discloses an apparatus that is adapted to form microspheres by individually enveloping falling droplets of a polyanion solution with a collapsing annular sheet of a polycation solution while the sheet is traveling downwardly at the same velocity as the droplets. The apparatus includes an oscillator to produce the droplets and a means for deflecting a certain number of droplets to obtain an optimum ratio of polyanion droplets to polycation to produce uniform spheres.

U.S. Pat. No. 6,458,296 discloses a device that is adapted to divide an immobilization mixture into equal parts by superimposition of an external vibration. The device includes a metal ring having a through hole. The metal ring is mounted downstream from a nozzle with the nozzle axis extending through the through hole. The metal ring is connected to a high-voltage source that produces an electrical field between the metal ring and the nozzle. During use, an encapsulation mixture comprising an immobilization matrix and cells or substances is conveyed through the nozzle in such a way that a free laminar jet is produced. By virtue of a vibration being superimposed on the free jet, the free jet is broken up into drops of equal size. When the fluid penetrates into the electrical field, a charge flux occurs in the direction of the nozzle so that the separated drops have an electrostatic charge. This charge causes mutual repulsion of the drops. Consequently, the small radial displacements between the drops are increased and the single-strand chain of drops is expanded to form a cone of drops. These drops fall into a hardening bath to form particles. The charges of the drops are removed by grounding of the hardening bath.

U.S. Pat. No. 6,649,384 discloses a method and a system for the encapsulation of viable biological material with a polymeric material to form a gelled capsule, which preferably can be transplanted into genetically dissimilar hosts. The method includes an electrostatic mixing process for producing encapsulated cell clusters with at least two polymeric coatings. The system includes a spinning disc atomizer. Biological material is encapsulated in a first alginate layer and the resultant capsules are suspended in a liquid carrier medium such as a saline solution. An electrostatic charge is applied to the carrier medium which is then introduced into an alginate solution, and the resultant suspension is atomized and gelled to form a second alginate layer.

However, there remains a need for an alternative system that allows encapsulation of cells in a controlled, reproducible and economical manner.

SUMMARY OF THE INVENTION

According to an aspect of the invention, there is provided an apparatus for encapsulating cells. The apparatus includes a dipping mechanism that is attachable to a dispenser for dispensing a cell suspension. The dipping mechanism is adapted to dip an outlet of the dispenser in an encapsulation solution to allow the cell suspension dispensed thereat to come into contact with the encapsulation solution.

According to another aspect of the invention, there is provided an apparatus for encapsulating cells which apparatus includes a dispenser for dispensing a cell suspension into an encapsulation solution through an outlet thereof. The dispenser comprises a fluid container for containing a cell suspension. This fluid container has a moving member wherein the dispenser is adapted such that the moving member of the fluid container is separable from the cell suspension by a displacement fluid. The apparatus of this aspect of the invention also comprises a dispensing tip that defines the outlet of the dispenser and a feed line that connects the fluid container to the dispensing tip. In one embodiment of this aspect, the apparatus further comprises a pumping means that pumps the displacement fluid present in the fluid container into the feed line for indirectly dispensing the cell suspension therein.

Other aspects and advantages of the invention will become apparent from the following detailed description, taken in conjunction with the accompanying drawings, illustrating by way of example the principles of the invention.

BRIEF DESCRIPTION OF DRAWINGS

FIGS. 4-9 are schematic drawings of dipping mechanisms, according to alternative embodiments of the invention;

FIG. 10 is a drawing of a plan view of the support in FIG. 3, showing a vessel received and supported therein;

FIG. 11 is a drawing of a plan view of an alternative support that can be used with the apparatus in FIG. 1;

FIG. 12 is an isometric drawing of a wafer substrate having a plurality of cavities, each of which defines a vessel;

DETAILED DESCRIPTION OF THE EMBODIMENTS

Figure 1:
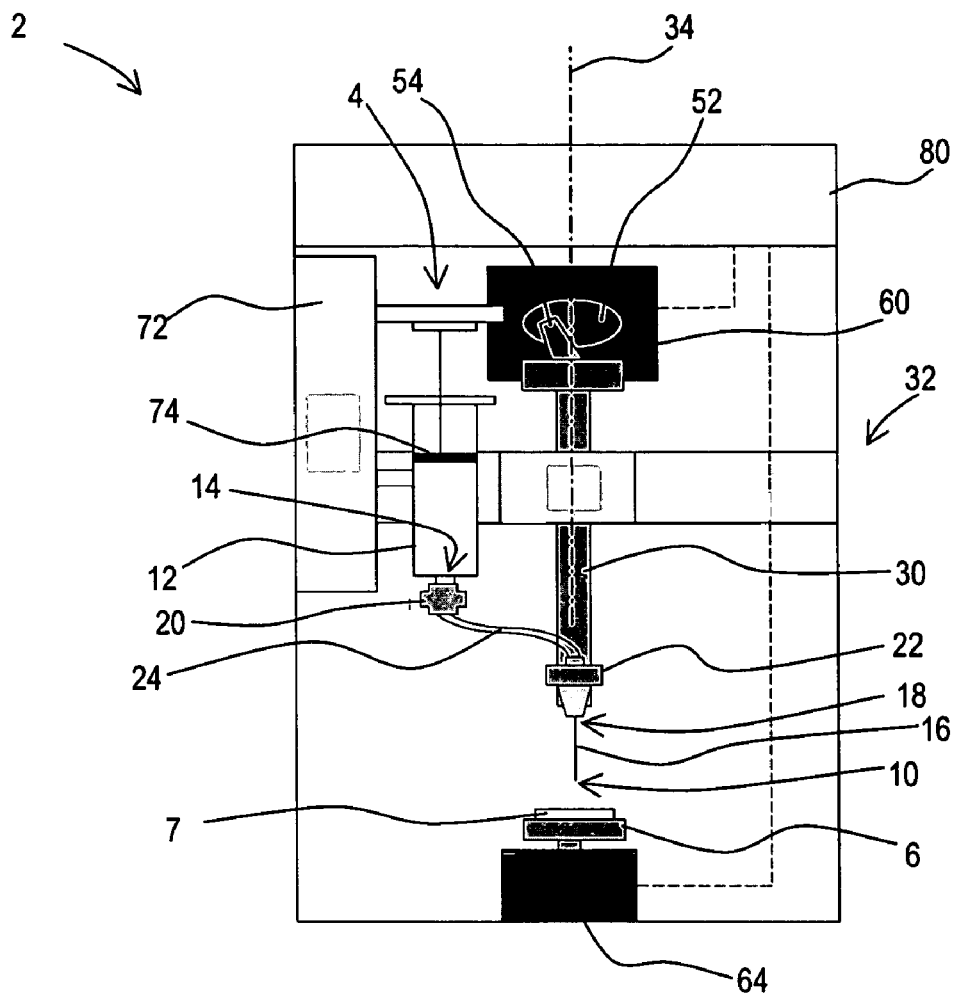
FIG. 1 is a schematic drawing of an apparatus for encapsulating cells, according to an embodiment of the invention.

It is understood that the terminology and definitions used herein are for the purpose of describing particular embodiments of the invention only, and not intended to be limiting.

The term "cell" as used herein refers to any type of cell that is suitable for encapsulation with a polymer membrane such as a polyelectrolyte based membrane. The cell can be any prokaryotic or eukaryotic cell.

Examples of prokaryotic cells which can be encapsulated using the apparatus of the invention include, but are not limited to *Serratia marcescens* (which can be encapsulated in polyelectrolyte complexes (PEC) prepared from sodium cellulose sulfate and poly(dimethyldiallylammonium chloride, for example).

Eukaryotic cells can be derived from lower organisms such as yeast or from higher species such as animal species. In case of animal species, the cells may preferably of mammalian origin, including human, and can be derived from any organ. The cell can also be a hybrid artificial cell, or any otherwise genetically modified cell such as PC 12 cells, OKT3 cells, or 3T3 fibroblasts, to new a few examples. Examples of such cells that can be encapsulated with the apparatus of the invention include hepatocytes or other liver cells, cells from other endocrine organs such as pancreatic cells (for example, insulin producing islet cells), kidney cells or thyroid cell. Other examples of cells include osteoblasts, fibroblasts, chondrocytes, antibody producing cells (for example B- or T-cells), or other cells of the immune system to name a few (see also Uludag, H. et al., Advanced Drug Delivery Reviews 42 (2000), 29-64). The term "cell" also includes any other active biological material that can be encapsulated. Examples of such material include fungi, helminthes, viruses, prions, naked DNA, larvae or other multicellular parasites as described in U.S. Pat. No. 6,531,156, for example.

The apparatus of the invention can be used for any known cell encapsulation technique in which cells are coated with a relatively thin coating by contacted cells or any other particulate material such as fungi, viruses etc. mentioned above.

The encapsulating reagent used in encapsulation methods that can be practiced with the apparatus of the invention is typically one or more polymer (material) that can be water soluble or water insoluble. Examples of encapsulation techniques that can be conveniently carried out using the apparatus of the invention include, but are not limited to, microencapsulation and macroencapsulation In macrocapsulation cells are enclosed between two or more selectively permeable flat sheet membranes or within the lumen of a semi-permeable hollow fiber (cf. Uludag et al., Advanced Drug Delivery Reviews 42(2000) 29-64). In microencapsulation a smaller cell mass or particle is individually entrapped in an essentially spherical polymer capsule (see for instance, Uludag et al., Advanced Drug Delivery Reviews 42(2000) 29-64, U.S. Pat. No. 6,531,156, or U.S. Pat. No. 5,620,883), wherein this polymer capsule may have a diameter $\varnothing$=of about 0.3 to about 1.5 mm, for example. Two commonly used techniques for cell encapsulation that can be practiced with the apparatus of the invention are complex coacervation and interfacial precipitation. Complex coacervation involves the electrostatic interaction of two oppositely charged polyelectrolytes. At the right matching charge density, the two polyions combine and migrate to form a colloid-rich or water-insoluble phase. The molecular weight and chain conformation parameters of the polyions may also play an important role in the complexation process. Interfacial precipitation relies simply on the solidification of a dissolved polymer upon contact with an aqueous phase.

The polymers used for the encapsulation can be biocompatible or if, for example, only in vivo studies are to be performed with the encapsulated cells, materials with no or very low biocompatibility. The polymers used can be of natural or synthetic origin.

Examples of naturally occurring polymers are collagen (which can be modified to be positively or negatively charged or galactosylated), chitosan or polyanionic alginate, to mention a few of polymers known in the art.

Examples of biocompatible synthetic polymers (polyelectrolytes) that can be used in the practice of this invention are polycationic poly(L-lysine) or acrylate polymers. Suitable acrylate polymers include acrylate polymers, copolymers and terpolymers such as poly(acrylic acid), poly(methacrylic acid) poly(methacrylate), poly(methyl methacrylate) and acrylate copolymers and terpolymers of acrylic acid, methacrylic acid, methacrylates, methyl methacrylates, hydroxyethyl methacrylic such as 2-hydroxyethyl methacrylate, hydroxypropylacrylate and the like, and blends thereof. One specific example of such an acrylate terpolymer consists of 25% hydroxyethyl methacrylate, 25% methacrylic acid and 50% methyl methacrylate. Copolymers or terpolymers of acrylic acid and/or methacrylic acid with 2-hydroxyethyl methacrylic and/or hydroxypropylacrylate and methacrylate and/or methyl methacrylate are further examples anionic synthetic polymers that can be used for encapsulation methods using the apparatus of the invention. Poly(dimethylaminoethyl methacrylate) ("DMAEMA") and copolymers and terpolymers of dimethylaminoethyl methacrylate with 2-hydroxyethyl methacrylate and/or hydroxypropylacrylate and methacrylate and/or methyl methacrylate are examples of cationic synthetic polymers.

The term "fluid medium" refers to any type of solution or cell suspension which comprises cells that are to be encapsulated. The encapsulation solution can be any encapsulation solution that is used normally used for this purpose.

According to some embodiments of the invention, an apparatus for encapsulating cells includes a dipping mechanism that is attachable to a dispenser for dispensing cells suspended in a fluid medium (cell suspension). The dipping mechanism is adapted to dip an outlet of the dispenser in an encapsulation solution to allow the cell suspension dispensed at the dispenser outlet to come into contact with the encapsulation solution. The dipping mechanism includes a dipping member that is attached to the dispenser outlet and an actuating means that is adapted to actuate the dipping member.

In some of these embodiments, the dipping member may include a plunger that is fixed to the dispenser outlet. The plunger is reciprocatable along an axis transverse to a plane of a support on which a vessel containing the encapsulation solution is supportable.

In some embodiments that include the plunger as a dipping member, the actuating means may include a motor and a movement translating member for translating the rotational movement of a shaft of the motor to axial movement of the plunger. The movement translating member may include a member that is fixed to the shaft of the motor to be thereby rotatable, and a link having a first end and a second end. The first end of the link is pivotably attached to the plunger and the second end of the link is pivotably attached to the rotatable member at an off-center position thereof to thereby allow the movement translation.

In some of the abovementioned embodiments, the apparatus may in addition to the dipping mechanism further include the dispenser for dispensing the cell suspension. The dispenser may include at least one dispensing tip, wherein the dispensing tip has an outlet that defines the outlet of the dispenser. Alternatively, the dispenser may include a syringe having an integral dispensing tip. The dispenser may also include a syringe, a dispensing tip separate from the syringe and a flexible feed line connecting the syringe to the dispensing tip. The flexible feed line is adapted for containing the cell suspension. The dispensing tip may in this case include a hollow needle, such as a disposable needle.

When a moving member of a dispenser directly pushes against the cell suspension to dispense it, the dispenser is referred to herein as a "direct-pumping" dispenser. When a moving member of a dispenser pushes against a displacement fluid that in turn pushes against the cell suspension to dispense the cell suspension, the dispenser is referred to herein as an "indirect-pumping" dispenser. In other words, in a direct-pumping dispenser, the moving member abuts the cell suspension whereas in an indirect-pumping dispenser, the moving member is separable from the cell suspension by a displacement fluid. Some dispensers may be used both as a directly pumping as well as an indirectly pumping dispenser.

For embodiments where the dispenser includes a syringe, the apparatus may further include pumping means for pumping the syringe. The syringe may be pumped using the pumping means to dispense the cell suspension at an at least substantially constant flow rate while the dipping mechanism dips the dispenser outlet. Alternatively, the syringe may be pumped in synchronization with the dipping motion of the dispenser outlet. For example, the syringe may be pumped to cause a drop of the cell suspension to be dispensed at the dispenser outlet before the dipping mechanism dips the dispenser outlet in the encapsulation solution. The syringe may be pumped again after the dipping mechanism lifts the dispenser outlet out of the encapsulation solution. In this manner, the syringe is pumped intermittently, i.e. when the dispenser outlet is lifted out of the encapsulation solution.

The syringe may be used as a direct or indirect pumping dispenser for dispensing the cell suspension. When used as a direct pumping dispenser, as referred to herein, a moving member of the syringe, in this case a piston or plunger, is in direct contact with the cell suspension. The movement of the plunger thus directly pushes the cell suspension to dispense it. When used as an indirect pumping dispenser, as referred to herein, a displacement fluid separates the cell suspension from the plunger. The movement of the plunger directly pushes against the displacement fluid to thereby cause the cell suspension adjacent the displacement fluid to be dispensed. The plunger is not in direct contact with the cell suspension.

The displacement fluid may be air or any fluid that do not mix at all or only to a negligible extent with the cell suspension during pumping/dispensing. Another example of an indirect pumping dispenser is a pressure driven pump, wherein pressure of the gas therein can be regulated to dispense the cell suspension. One example of a suitable pressure driven pump is an pneumatic pump, which can be an air-exhausting or forcing pump. A peristaltic pump may also be used as a direct or indirect dispenser.

For dispensers including a syringe, the dispensers may each further include a valve connected between the syringe and the flexible feed line to fluidically connect the syringe to the flexible feed line. The valve includes an inlet and an outlet, wherein the valve inlet is connected to the syringe outlet and the valve outlet is connected to an input end of the flexible feed line. The valve may include a second inlet for receiving the cell suspension.

The operation of the valve can be performed manually or can be automated. In the latter case, a "one way-valve" can be used to automatically alternate between drawing the cell suspension into the flexible feed line and dispensing the cell suspension. In case of such an automated operation, the drawing of the cell suspension and dispensing will depend on the syringe attached to the pump for infusion and withdrawal. Any suitable automated "one-way valve" can be used for this purpose. One example of such a suitable valve is a check valve. Most check valves rely on the use of a ball of a certain diameter that sits freely above a seat containing a single through-hole with a diameter slightly smaller than that of the ball. Fluid should not pass the check valve in any way but through the seat. When the pressure behind the seat exceeds that above the ball, fluid flows through the valve. When the pressure above the ball exceeds the pressure below the seat, the ball returns to rest in the seat, forming a seal and preventing fluid backflow.

In some of the embodiments, the apparatus may in addition to the dipping mechanism further include the support for supporting a vessel containing the encapsulation solution. The support may be rotatable using a second motor for providing some turbulence in the encapsulation solution. In such a case, the dispenser outlet may be dipped into the vessel at a position that is off the axis of rotation of the support, i.e. at an off-centered position. The dispenser output may be dipped several times in the vessel when the support rotates a single revolution to allow the dispensed drops of cell suspension to be deposited at different locations in the encapsulation solution contained in the vessel. In other words, the dipping rate of the dispenser outlet may be several times higher than the speed of rotation of the support. Alternatively or additionally, the support may be gently vibrated or tilted. As another example, the encapsulation solution may be flowed or circulated to allow dispensed drops of cell suspension to be deposited in fresh or recirculated encapsulation solution.

According to other embodiments of the invention, an apparatus for encapsulating cells includes an indirect-pumping dispenser for dispensing a cell suspension into an encapsulation solution through an outlet thereof. An example of an indirect-pumping dispenser is the above-described syringe. Other examples include, but are not limited to, a pressure driven pump and a peristaltic pump. In some of these other embodiments, the apparatus further includes a dipping mechanism attached to the dispenser outlet for dipping the dispenser outlet in the encapsulation solution to allow the cell suspension dispensed thereat to come into contact with the encapsulation solution.

Figure 2:
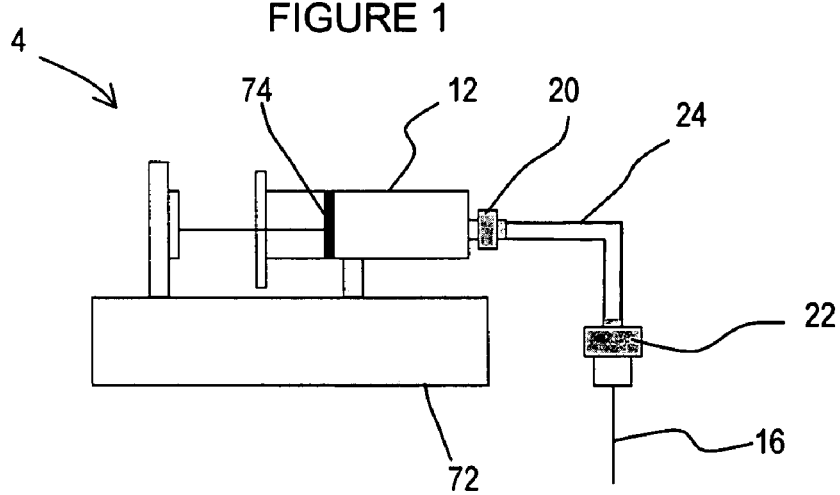
FIG. 2 is a schematic drawing of a dispenser of the apparatus in FIG. 1.
Figure 3:
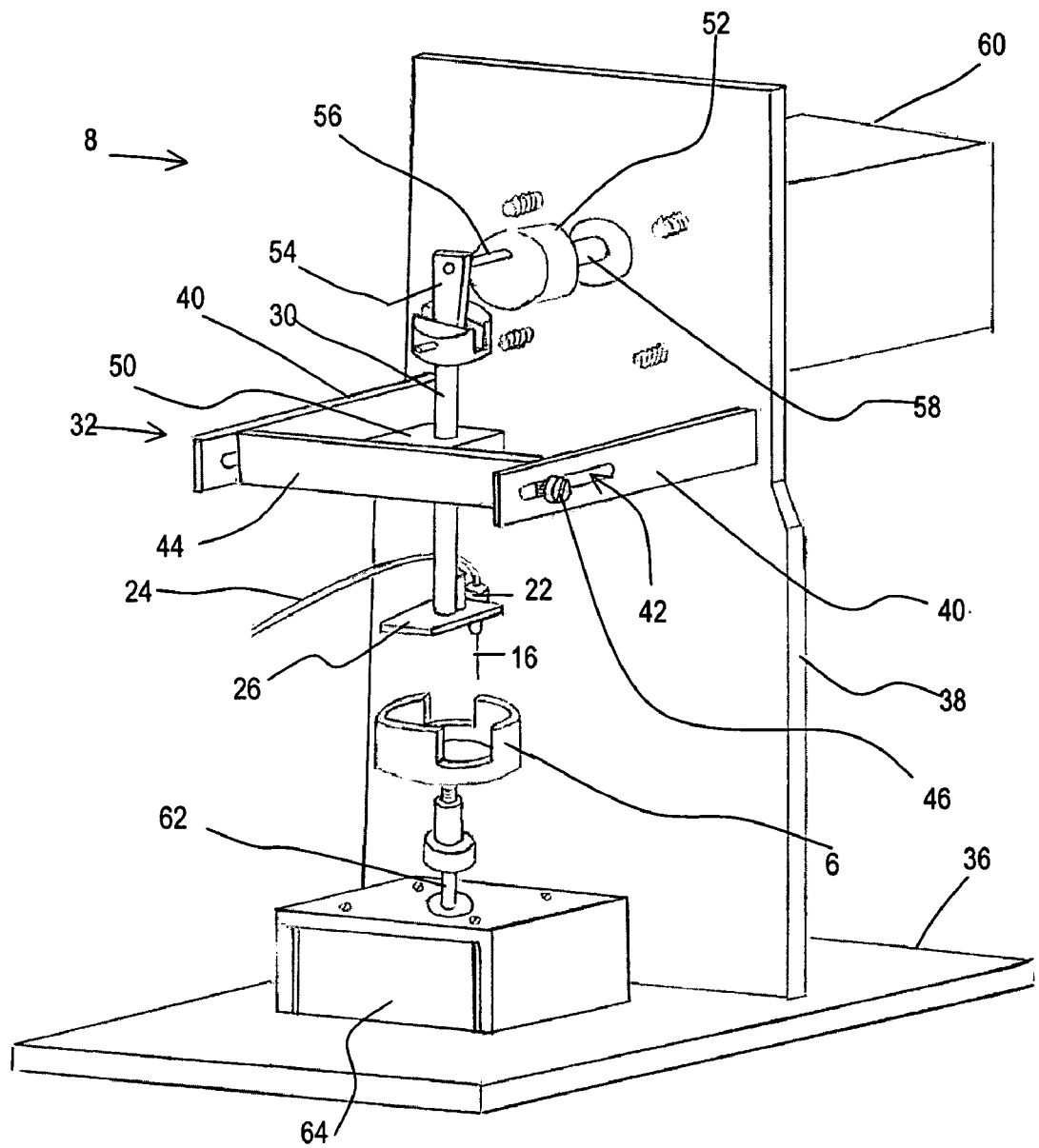
FIG. 3 is an isometric drawing of a dipping mechanism and a support of the apparatus in FIG. 1.

Referring to FIGS. 1-3, an apparatus 2 according to one specific embodiment of the invention is next described. The apparatus includes a dispenser 4 for dispensing a cell suspension (not shown), a chamber holder or support 6 for supporting a vessel 7 containing an encapsulation solution (not shown), and a dipping mechanism 8. The dispenser 4 has an outlet 10 from which the cell suspension is dispensed. The dipping mechanism 8 is attached to the dispenser outlet 10 for reciprocating the dispenser outlet 10 towards and away from the support 6 for dipping the dispenser outlet 10 into the vessel 7 supportable on the support 6 to thereby allow the cell suspension dispensed at the dispenser outlet 10 to come into contact with the encapsulation solution contained in the vessel 7.

In this embodiment, the dispenser 4 includes a syringe 12 having an outlet 14; a hollow needle 16 having an inlet 18, and an outlet 10 that defines the dispenser outlet 10; a valve such as a stopcock 20; an adapter such as a luer lock 22; and a flexible feed line 24. The adapter may alternatively be RECORD and ROCOF locks, for example. The hollow needle 16 may for example be a disposable needle. The use of disposable needles prevents contamination. The flexible feed line 24 may for example be a flexible tubing of about, but not limited to, ten centimeters long. The stopcock 20 connects the syringe outlet 14 to an input end of the flexible feed line 24. The luer lock 22 connects the output end of the flexible feed line 24 to the hollow needle inlet 18. In this manner the hollow needle 10 is fluidically connected to the syringe 12.

In this embodiment, the dipping mechanism 8 includes a dipping member such as a plunger 30 that is fixed to a holder 26. The luer lock 22 is mounted to this holder 26. In this manner, the hollow needle 16 is substantially fixed to the plunger 30 to be moveable therewith. The plunger 30 is supported by a guiding structure 32 to be moveable along an axis 34 of reciprocation that is transverse, for example perpendicular, to a plane of the support 6. The guiding structure 32 includes a base 36, a wall 38 that extends from the base 36, two arms 40 which extend from the wall 38 parallel to a plane of the base 36. Each arm 40 includes an elongated slot 42 defined therein. The guiding structure 32 further includes a cross beam 44 that is mounted between the two arms 40. This cross beam 44 is moveable along the length of the arms 40 so that its distance from the wall 38 is adjustable. When moved to a desired position, the ends of the cross beam 44 are bolted to the respective arms 40 using bolts 46 that extend through the slots 42 in the two arms 40. Fixed to the cross beam 44 is a guide block 50 that has a through hole defined therein. The plunger 30 is inserted through this through hole in the guide block 50 to be supported by the guide block 50. The axis of the through hole thus defines the axis 34 of reciprocation of the plunger 30.

In this embodiment, the dipping mechanism 8 has a movement translating member that includes a rotatable member such as a disc 52 and a link 54. One end of the link 54 is pivoted to an off-centered position on the disc 52 via an elongated pin 56. The link 54 is slideable along the elongated pin 56. The other end of the link 54 is pivoted to the plunger 30. In this manner, the link 54 connects the plunger 30 to the disc 52. The disc 52 is fixed to a shaft 58 of a first motor 60 that is mounted to the wall 38. With such an arrangement, the rotating motion of the disc 52 is translated to an axial motion of the plunger 30 for dipping the dispenser outlet 10. In this manner, the dispenser outlet 10 may be periodically lowered towards and raised from the support 6.

The support 6 is fixed to a shaft 62 of a second motor 64 mounted to the base 36. The support 6 is thus rotatable about an axis of rotation for providing some turbulence in the encapsulation solution. The position of the cross beam 44 is adjusted such that the dispenser outlet 10 is moveable along an axis, parallel to the axis 34 of reciprocation of the plunger 30, wherein the movement axis of the dispenser outlet 10 is offset from the axis of rotation of the support 6. In this manner, the dispenser output 10 may be dipped into the vessel 7 supported on the support 6 at a location away from the centre of the vessel 7. At a dipping rate greater than the speed of rotation of the support 6, the dispenser output 10 may be dipped several times into the vessel 7 when the support 6 is rotated a single revolution to thereby allow dispensed drops of the cell suspension to be placed at different locations in the vessel 7. These locations form a circular locus 70 in the vessel 7 as shown in FIG. 10. The frequency of dipping of the dispenser outlet 10 may be several times higher than the speed of rotation of the support 6 to obtain such a circular locus 70 when the support 6 is rotated a single revolution. Alternatively or additionally, the support 6 may be vibrated or tilted.

During use, the syringe 12 is mounted to a pumping means, such as a syringe pump 72, with a plunger 74 of the syringe 12 extended so that air is drawn into the syringe 12 to function as a displacement fluid. The rate of pumping by the syringe pump 72 is adjusted to correspond to a desired flow rate at which the cell suspension is to be dispensed. The speed of rotation of the motors 60, 64 can also be adjusted to provide a desired dipping rate of the dipping mechanism 8 and a desired speed of rotation of the support 6. The cell suspension to be encapsulated, for example with a charged polyelectrolyte, is introduced into the flexible feed line 24. The cell suspension may be obtained by first filling the flexible feed line 24 with a fluid medium (not shown) and then introducing the test sample of cells (not shown) into the flexible feed line 24 to be mixed with the fluid medium. Alternatively, the cell (test) sample may be introduced into the flexible feed line 24 to partially fill the feed line 24, with the fluid medium only introduced subsequently. It is also possible to fill the flexible feed line 24 with both the fluid medium and the test sample of cells simultaneously.

A vessel 7 containing the encapsulation solution is placed on the support 6. The disc 52 is manually rotated such that the dispenser outlet 10 is at its lowest point closest to the support 6. The position of the support 6 along the shaft 62 of the second motor 64 is then adjusted such that at this lowest position of the dispenser outlet 10, the dispenser outlet 10 is able to dip into the encapsulation solution in the vessel 7.

The syringe pump 72 and the motors 60, 64 are then activated. The motors 60, 64 may be activated using a controller 80 that includes drivers, potentiometers and speed indicators (all not shown) to allow the speed of the motors 60, 64 to be set and monitored. As the cell suspension dispensed at the dispenser outlet 10 is dipped in the encapsulation solution contained in the vessel 7, it becomes detached from the dispenser outlet 10 to be encapsulated in the encapsulation solution to form a gelled capsule 81 (compare FIG. 13). Due to the centrifugal force exerted on the encapsulation solution, the capsule 81 is able to leave the location or spot in the encapsulation solution at which it is deposited to drift towards the outer wall of the vessel 7, clearing the way for another capsule 81 to be deposited. In other words, with the off-center dipping of the dispenser outlet 10, it is unlikely that all the formed capsules 81 are located at about the same spot in the encapsulation solution to overlap with each other. This allows the capsules 81 to be spread out in the encapsulation solution.

Advantageously, the apparatus that embodies the invention allows encapsulation of cells with a very low level of expenditure in terms of material and time. For example, the volume of encapsulation solution that is required may be as low as 2 ml and the volume of a cell suspension drop that is encapsulated may be as low as 100 μl. With such small drop sizes, the batch size of cell suspensions may be below 1 ml, thus reducing consumption of valuable cell samples. In the apparatus, sterility is relatively easily maintained as the cell suspension can be injected through the 2-way stopcock, and the cell suspension is separated from the syringe plunger by the displacement fluid. Flushing of the cell suspension from the apparatus is also possible through the stopcock. Sterility can be further improved by changing the flexible feed line and disposable needle after each use, a task which can be performed relatively easily when using the apparatus. The cells that are encapsulated are unlikely to be damaged since no high voltage, vibration or organic solvents are involved.

The apparatus may be used for encapsulating cells for several different applications. For example, the apparatus may be used for encapsulating cells such as hepatocytes for use in a bioreactor which may be implanted in patients with liver failure to function as a bioartificial liver-assisted device. The apparatus may also be used for encapsulating cells for three dimensional cell culture studies or three dimensional imaging, for cell protection during cryopreservation, and for drug testing and screening.

Although the invention is described as implemented in the above-described embodiments, it is not to be construed to be limited as such. For example, other dipping mechanisms may be used with the apparatus 2 in place of the dipping mechanism 8 described above. FIG. 4 shows one such dipping mechanism 8a. This dipping mechanism 8a includes the above described plunger 30 and a cam 82 as an actuating means. The cam 82 has a circumferential surface 83 that is used to directly move the plunger 30. The plunger 30 is biased away from the support 6 by a coil spring 84 to abut the circumferential surface 83 of the cam 82. As the cam 82 is rotated, the plunger 30 is then pushed, against the biasing force of the coil spring 84, to be thereby moveable along the axis 34 towards the support 6.

FIG. 5 shows another dipping mechanism 8b. This dipping mechanism 8b includes the plunger 30 described above. The actuating means of this dipping mechanism 8b includes a pump 90, such as but not limited to a hydraulic pump and a pneumatic pump. The plunger 30 is biased to abut the pump 90 to be moveable when the pump 90 is activated.

FIG. 6 shows yet another dipping mechanism 8c that includes a plunger 30a having a magnetic portion 92. The actuating means includes a solenoid 94 through which the magnetic portion 92 of the plunger 30a is inserted. An alternating current source 96 is connected to the solenoid 94 to activate the solenoid to reciprocate the plunger 30a.

Figure 7:
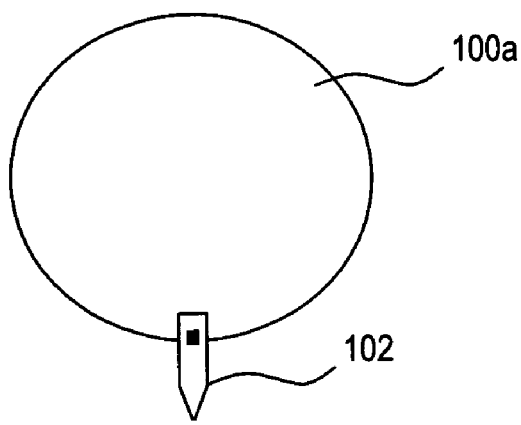
Figure 8:
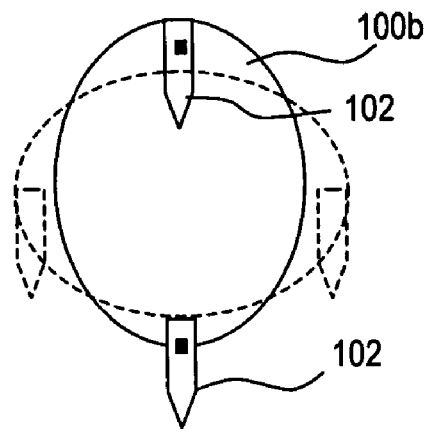
Figure 9:
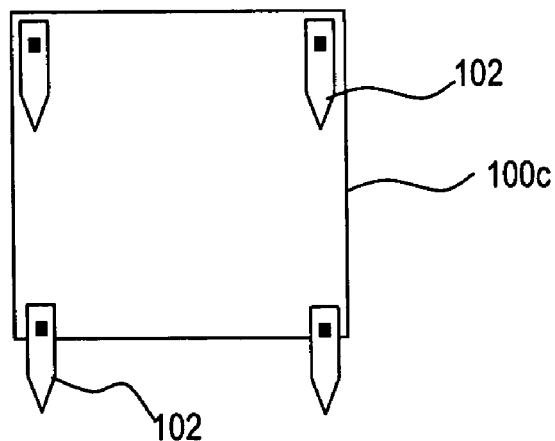

Other non-plunger types of dipping mechanisms may also be used. FIGS. 7, 8 and 9 show three dipping members of such dipping mechanisms. These dipping members may include a plate 100a, 100b, 100c to which one or more dispensing tips 102 is pivotably attached at a position thereon that is offset from an axis of rotation of the plate 100a, 100b, 100c. The plates may be oval, circular and polygonal in shape as shown in FIGS. 7, 8 and 9. With such dipping members, each dispensing tip is dragged across the encapsulation solution more to allow easier detachment of cell suspension drops dispensed thereat.

As another example, the support 6 may include holding means, such as bolts inserted through the wall of the support 6 to be angularly spaced apart from each other. These bolts may be screwed into and out of a cavity 110 of the support 6 by different lengths for receiving vessels, such as vessel 7a, such that it is positioned off-centered in the cavity 110 of the support 6.

As yet another example, one of any of the dipping mechanisms and a support may be moveable relative to the other which is fixed, for example using an X-Y table (not shown) to thereby allow the dispenser outlet to be dipped into the vessel 7 at different positions in the vessel 7. In such a case, the support 6 may be used to support a substrate 120 such as a wafer substrate or an ELISA plate that includes multiple cavities 124 containing the encapsulation solution. This embodiment can be easily employed for bioanalytical, biopharmaceutical or drug screening or testing purposes or to create desired cells patterns on a given substrate. This example also makes clear that the apparatus of the invention only comprises the dipping mechanism that is attachable or attached to a dispenser for dispensing a cell suspension as defined above and can be used with any substrate and/or vessel that contains an encapsulation solution, wherein this vessel and the substrate are not part of the apparatus of the invention.

EXAMPLES

The apparatus 2 allows cell encapsulations in a manner similar to manual extrusion of immobilization mixtures such as positively charged collagen into hardening polyelectrolyte terpolymers solutions of methylacrylic acid (MAA), hydroxyethylmethacrylate (HEMA) and methylmethacrylate (MMA), for example, through complex coacervation. Complex coacervation involves the electrostatic interaction of two oppositely charged polyelectrolytes. At the right matching charge density, the two charged polyelectrolytes combine and migrate to form a water-insoluble phase. Experiments using the apparatus for the encapsulation of heptatocytes and the respective results obtained are described next.

For the encapsulation of heptatocytes, modified collagen was used which was prepared as follows. Cationic collagen (Vitrogen 100, Collagen Corp., Palo Alto, Calif.) was obtained through the modification of the carboxyl group by esterification with low molecular weight alcohol as described in Chia et al. for example (Tissue Engineering, 2000, Vol. 6(5), P. 481-495). Briefly, a total of 20 ml of stock solution (3 mg/ml) of collagen (Vitrogen 100, Collagen Corp., Palo Alto, Calif.) can first be precipitated with 400 ml of acetone. The precipitated collagen is dissolved in 200 ml of 0.1 M HCl containing methanol (Merck), and stirred at 4° C. for 6 days under sterile conditions. The modified collagen solution is then dialyzed against distilled water for an additional 4 days at 4° C. followed by freeze-drying. The lyophilized modified collagen can then be stored up to 6 months at −20° C. in the presence of desiccant. For the encapsulation experiments as described here, the modified collagen was used in a concentration of 1.5 mg/ml in 1× phosphate-buffered saline (PBS).

The terpolymer used consisted of 25% hydroxyethyl methacrylate, 25% methacrylic acid and 50% methyl methacrylate. For the encapsulation, a 1% solution (in 1×PBS) of the terpolymer was employed.

For encapsulation the heptatocytes suspended in minimal media were spun down by centrifugation. Then, collagen containing PBS (1.5 mg/ml collagen concentration) was added to the cell pellet and the cells were gently resuspended with a pipette to yield a density of $2.5 \times 10^6$ cells/ml. The so obtained cell suspension was then filled into a Dow corning Silastic tubing ID 1.02 mm used as flexible feed line 24. The cell suspension was then brought in contact with the terpolymer solution which was contained in the vessel 7 (a 35 mm culture dish) by using the dipping mechanism 8 and a BD needle 30½ G employed as hollow needle 16. As a result, capsules comprising a membrane formed by complex coacervation between the positively charged collagen and the negatively charged terpolymer were formed.

Figure 13:
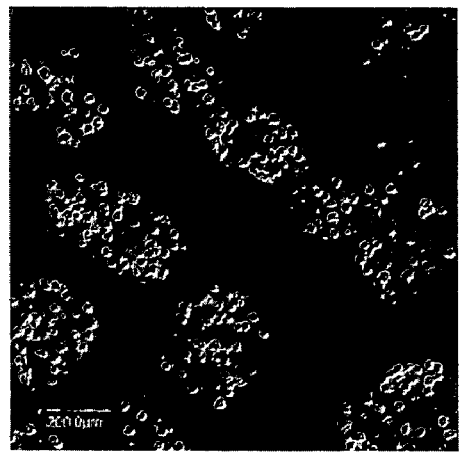
FIG. 13 is a photographic image of gelled capsules produced using the apparatus in FIG. 1.

FIG. 13 is an enlarged photograph showing the capsules produced using the apparatus. Both the flow rate of the cell suspension and the dipping rate of the dispenser outlet were varied to obtain different capsule sizes. The dipping rate was varied within the range of 200 and 800 dips/min, while the flow rate was varied between 10 μL/min and 50 μL/min. As mentioned, a BD needle 30 G ½ was used as the dispenser outlet 10 in order to allow for easy replacement.

Figure 14:
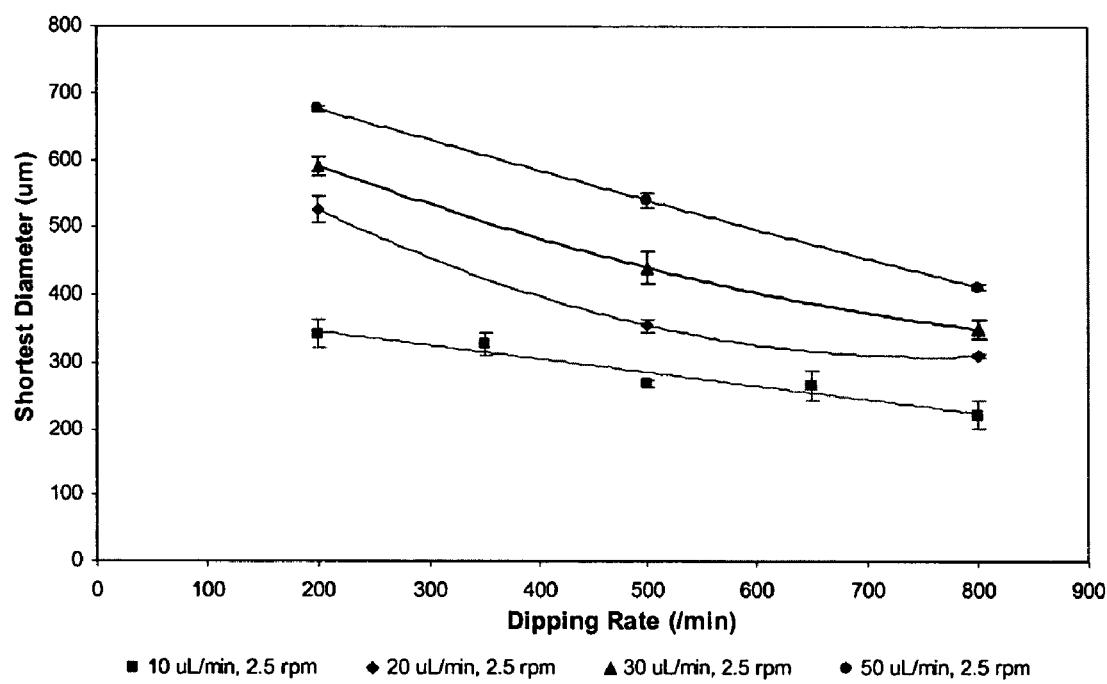
FIG. 14 is a graph showing the variation in the capsule size with a change in the dipping rate of the dipping mechanism for cell suspension dispensed at four different flow rates.

The experimental results are described next. FIG. 14 is a graph showing the variation of the capsule size with a change in the dipping rate of the dipping mechanism 8 for cell suspension dispensed at 10, 20, 30 and 50 μL/min with the support 6 rotated at a speed of 2.5 rpm. It can be seen from the graph that increased dipping rate reduces capsule size. The following equations, obtained via curve fitting, can be used for representing the average capsule diameters within appropriate ranges:

| | |
|---|---|
| $d = 4\text{E}{-}05 x_1^2 - 0.4844 x_1 + 771.11$ at | $x_2 = 50\ \mu\text{L/min};\ 412 \leq d \leq 676$ |
| $d = 0.0003\ x_1^2 - 0.7406\ x_1 + 725.56$ | $x_2 = 30\ \mu\text{L/min};\ 350 \leq d \leq 591$ |
| $d = 0.0007\ x_1^2 - 1.06\ x_1 + 710$ | $x_2 = 20\ \mu\text{L/min};\ 310 \leq d \leq 526$ |
| $d = -2\text{E}{-}06\ x_1^2 - 0.2002\ x_1 + 385.97$ | $x_2 = 10\ \mu\text{L/min};\ 222 \leq d \leq 343$ | where $d$=diameter of capsule in μm;

$x_1$=dipping rate in dips/min; and $x_2$=flowrate in μL/min.

Figure 15:
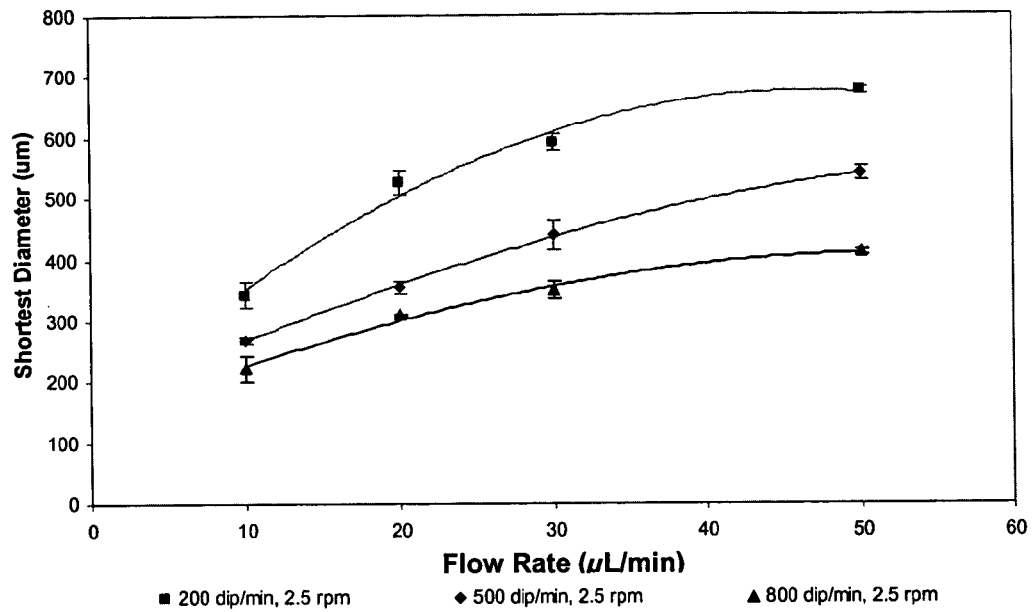
FIG. 15 is a graph showing the variation of the capsule size with a change in the flow rate of the cell suspension for three dipping rates of the dipping mechanism.

FIG. 15 is a graph showing the variation of the capsule size with a change in the flow rate of the cell suspension for dipping rates of 200, 500 and 800 dips/min of the dipping mechanism 8 with the support 6 rotated at a speed of 2.5 rpm. It can be seen from this graph that the size of capsules increases with an increase in the flow rate of the cell suspension. The following equations, obtained via curve fitting, can be used for representing the average capsule diameters within appropriate ranges:

| | |
|---|---|
| $d = -0.2395\ x_2^2 + 22.422\ x_2 + 150.8$ at | $x_1 = 200$ dips/min; $343 \leq d \leq 676$ |
| $d = -0.0823\ x_2^2 + 11.793\ x_2 + 156.78$ | $x_1 = 500$ dips/min; $268 \leq d \leq 540$ |
| $d = -0.0968\ x_2^2 + 10.446\ x_2 + 130.65$ | $x_1 = 800$ dips/min; $222 \leq d \leq 412$ | where $d$=diameter of capsule in um;

$x_1$=dipping rate in dips/min; and $x_2$=flow rate in μL/min.

From the results obtained, it is found that the batches of capsules can be reproduced using the apparatus of the invention with standard deviation below 10%, while the size distribution within a batch is below 20%.

Figure 16:
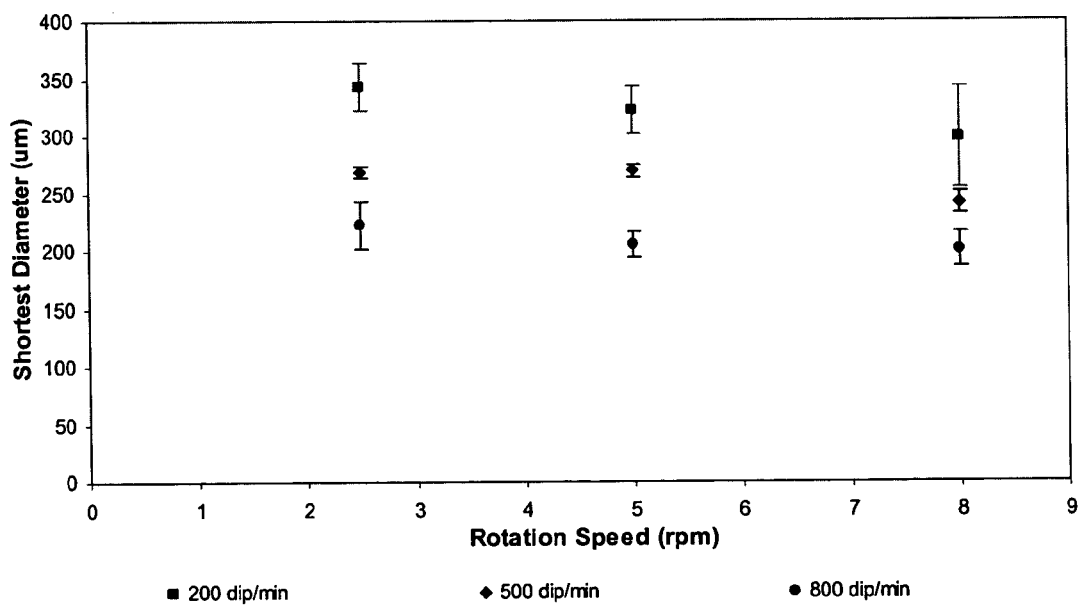
FIG. 16 is a graph showing the variation of the degree of elongation of capsules with a change in the rotation speed of the support in FIG. 1 for three dipping rates of the dipping mechanism.

Variation of capsule size with variation in base rpm. FIG. 16 is a graph showing the variation of the degree of elongation of capsule with a change in the rotation speed of the support 6 for dipping rates of the dipping mechanism 8 of 200, 500 and 800 dips/min, with the flow rate maintained at 10 μL/min. The degree of elongation of a capsule is defined as:

$$\frac{(\text{longest\_diameter\_of\_the\_capsule} - \text{shortest\_diameter\_of\_the\_capsule})}{(100)}$$

It can be seen from the graph that the degree of elongation increases with an increase in the rotation speed of the support 6 from 2.5 rpm to 8 rpm, especially for bigger capsules formed at 200 dips/min. The greater the degree of elongation, the more elongated the capsule shape is, i.e., the less spherical the capsule shape is.

Accordingly, the apparatus that embodies the invention allows the encapsulation of cells in a very controlled, reproducible and economical manner, making it a promising apparatus for biomedical and other applications.

What is claimed is:

1. An apparatus for encapsulating cells comprising:
    a dipping mechanism that is attachable to a dispenser for dispensing a cell suspension, wherein the dipping mechanism is adapted for dipping an outlet of the dispenser with a cell suspension dispensed at the outlet of the dispenser in an encapsulation solution to allow the cell suspension dispensed thereat to come into contact with the encapsulation solution wherein the dipping mechanism comprises a dipping member which is attached to the dispenser outlet and an actuating means that is adapted to actuate the dipping member, and wherein the dipping mechanism is adapted to lift the outlet of the dispenser out of the encapsulation solution after detaching the cell suspension dispensed at the outlet of the dispenser and after dipping the outlet therein in the encapsulation solution.

2. An apparatus according to claim 1, wherein the dipping member comprises a plunger that is fixed to the dispenser outlet and that is reciprocatable along an axis transverse to a plane of a support on which a vessel containing the encapsulation solution is supportable.

3. An apparatus according to claim 2, wherein the actuating means comprises:
    a motor for moving the plunger; and
    a movement translating member for translating the rotational movement of a shaft of the motor to axial movement of the plunger.

4. An apparatus according to claim 3, wherein the movement translating member comprises:
    a member that is fixed to the shaft of the motor to be thereby rotatable;
    a link having a first end and a second end, wherein the first end is pivotably attached to the plunger and the second end is pivotably attached to the rotatable member.

5. An apparatus according to claim 3, wherein the movement translating member comprises a cam having a circumferential surface and wherein the plunger is biased to abut the circumferential surface of the cam to be thereby moveable along the axis when the cam is rotated.

6. An apparatus according to claim 2, wherein the actuating member is one of a hydraulic pump and a pneumatic pump, and wherein the plunger is biased to abut the pump.

7. An apparatus according to claim 2, wherein the plunger has a magnetic portion, and wherein the actuating member comprises:
    a solenoid through which the magnetic portion of the plunger is inserted; and an alternating current source that is connected to the solenoid.

8. An apparatus according to claim 1, wherein the dipping member comprises a rotatable plate to which the dispenser outlet is pivotably attached at a position thereon that is offset from an axis of rotation of the plate.

9. An apparatus according to claim 8, wherein the plate has a shape that is one of an oval, a circular, and a polygonal shape.

10. An apparatus according to claim 1, further comprising the dispenser for dispensing the cell suspension.

11. An apparatus according to claim 10, wherein the dispenser comprises at least one dispensing tip having an outlet that defines the outlet of the dispenser.

12. An apparatus according to claim 10, wherein the dispenser comprises an indirect pumping dispenser.

13. An apparatus according to claim 10, wherein the dispenser comprises a syringe having an integral dispensing tip.

14. An apparatus according to claim 10, wherein the dispenser comprises:
   a syringe;
   a dispensing tip; and
   a flexible feed line connecting the syringe to the dispensing tip, the flexible feed line being adapted for containing the cell suspension.

15. An apparatus according to claim 14, wherein the dispensing tip comprises a hollow needle.

16. An apparatus according to claim 14, further comprising a pumping means for pumping the syringe.

17. An apparatus according to claim 16, wherein the pumping means pumps the syringe to dispense the cell suspension at an at least substantially constant flow rate.

18. An apparatus according to claim 17, wherein the syringe contains a displacement fluid which is pumped into the flexible feed line for indirectly dispensing the cell suspension therein.

19. An apparatus according to claim 14, further comprising a valve that is connected between the syringe and the feed line to fluidically connect the syringe to the flexible feed line.

20. An apparatus according to claim 19, wherein the valve has an inlet for receiving the cell suspension.

21. An apparatus according to claim 10, wherein the dispenser comprises a peristaltic pump.

22. An apparatus according to claim 2, further comprising the support for supporting the vessel containing the encapsulation solution.

23. An apparatus according to claim 22, wherein one of the dipping mechanism and the support is moveable relative to the other to thereby allow the dispenser outlet to be dipped into the vessel at different positions in the vessel.

24. An apparatus according to claim 22, wherein the support is rotatable.

25. An apparatus according to claim 24, wherein the dispenser outlet is arranged to dip into the vessel at different locations in the vessel as the support is rotated.

26. An apparatus according to claim 25, wherein the support further comprises holding means for holding the vessel in an off-centered position of the support.

27. An apparatus for encapsulating cells comprising:
   a dispenser for dispensing a cell suspension into an encapsulation solution through an outlet thereof, wherein a dipping mechanism is adapted to lift the outlet of the dispenser out of the encapsulation solution after detaching the cell suspension dispensed at the outlet of the dispenser and after dipping the outlet therein in the encapsulation solution, and wherein the dispenser comprises
   a fluid container for containing a cell suspension, the fluid container having a moving member wherein the dispenser is adapted such that the moving member of the fluid container is separable from the cell suspension by a displacement fluid;
   a dispensing tip defining the outlet of the dispenser,
   a dipping mechanism attached to the dispenser outlet for dipping the dispenser outlet in the encapsulation solution to allow the cell suspension dispensed thereat at the outlet of the dispenser to come into contact with the encapsulation solution, and a
   feed line connecting the fluid container to the dispensing tip.

28. An apparatus according to claim 27, wherein the dispenser comprises:
   a syringe as first fluid container;
   a dispensing tip; and
   a flexible feed line connecting the syringe to the dispending tip, the flexible feed line being adapted for containing the cell suspension.

29. An apparatus according to claim 28, further comprising a pumping means for pumping the syringe.

30. An apparatus according to claim 29, wherein the pumping means is adapted to pump the syringe to dispense the cell suspension at an at least substantially constant flow rate.

31. An apparatus according to claim 30, wherein the syringe contains a displacement fluid which is pumped into the flexible feed line for indirectly dispensing the cell suspension therein.

* * * * *